(12) United States Patent
Frach (10) Patent No.: US 7,741,607 B2
(45) Date of Patent: Jun. 22, 2010

(54) MODULAR SIGNAL PROCESSING BACKBONE FOR PET

(75) Inventor: Thomas Frach, Aachen (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 208 days.

(21) Appl. No.: 11/997,409

(22) PCT Filed: Jul. 27, 2006

(86) PCT No.: PCT/IB2006/052582

§ 371 (c)(1),
(2), (4) Date: Jan. 31, 2008

(87) PCT Pub. No.: WO2007/015198

PCT Pub. Date: Feb. 8, 2007

(65) Prior Publication Data

US 2009/0127467 A1 May 21, 2009

Related U.S. Application Data

(60) Provisional application No. 60/595,772, filed on Aug. 4, 2005.

(51) Int. Cl.
*G01T 1/164* (2006.01)
(52) U.S. Cl. .................................. 250/363.03
(58) Field of Classification Search ............ 250/363.03, 250/363.04, 363.09, 369, 370.08, 370.09, 250/370.1
See application file for complete search history.

(56) References Cited

U.S. PATENT DOCUMENTS

| | | | |
|---|---|---|---|
| 5,241,181 A * | 8/1993 | Mertens et al. | 250/363.03 |
| 6,346,706 B1 * | 2/2002 | Rogers et al. | 250/363.04 |
| 6,803,579 B2 * | 10/2004 | Williams et al. | 250/363.03 |
| 2001/0017352 A1 | 8/2001 | Stark | |
| 2004/0036025 A1 | 2/2004 | Wong et al. | |
| 2004/0195512 A1 | 10/2004 | Crosetto | |
| 2007/0096027 A1 * | 5/2007 | McParland | 250/363.03 |

FOREIGN PATENT DOCUMENTS

JP 2003050218 2/2003

OTHER PUBLICATIONS

Marino, et al. "Data Management for Real-Time Fully 3-D Tomograph Parallel Processing," Electrotechnical Conference 1996, 1996, 8th Mediterranean. vol. 2; pp. 1063-1066.

* cited by examiner

*Primary Examiner*—David P Porta
*Assistant Examiner*—Faye Boosalis (57) ABSTRACT

An imaging system (2) having a scalable event processing architecture includes a plurality of detector modules (4) arranged around an associated imaging region (8) to detect radiation events emitted from a subject disposed within the imaging region (8); a plurality of sets of processing elements (6), each set including processing elements of at least one of the plurality of radiation detector modules (4), each processing element (6) time-stamping an associated detected radiation events; and inserting the time-stamped event into a chronological position within a data stream (10) of events; and coincident detecting circuitry (22, 54) that receives the chronologically ordered stream of events and detects coincident pairs of events for use in reconstructing one or more associated images of the object.

23 Claims, 10 Drawing Sheets

MODULAR SIGNAL PROCESSING BACKBONE FOR PET

CROSS REFERENCE TO RELATED APPLICATIONS

This application claims the benefit of U.S. provisional application Ser. No. 60/595,772 filed Aug. 4, 2005, which is incorporated herein by reference.

The following relates to processing data. It finds particular application to time-sorting time-stamped data in medical imaging. More particularly, it time-sorts events detected by medical imaging systems, such as a Positron Emission Tomography (PET) scanner, in order to facilitate detection of coincident singles.

A conventional PET scanner has a plurality of radiation detector modules or heads. The modules are arranged to facilitate positioning a subject such that the modules surround the subject. A radiopharmaceutical is administered to and/or ingested by the subject. The radiopharmaceutical produces radiation decay events in the subject that emit positrons. The positrons travel a relatively short distance before interacting with an electron in an electron-positron annihilation event that produces two oppositely directed gamma rays. The two oppositely directed gamma rays are detected by two different radiation detector modules as two substantially simultaneous radiation detection events that define a line of response (LOR) therebetween.

Each radiation detector module includes electrical circuitry that determines spatial locations at which events are received and an energy of each event. Each radiation detector module often includes one or more scintillators that produce a burst or scintillation of light responsive to each gamma ray detection. In some PET scanners, an array of photomultiplier tubes (PMT's) optically coupled with the scintillators converts the light bursts into corresponding electrical signals. In other PET scanners, an array of photodiodes is used to produce analog electrical currents proportional to the intensity of the light bursts.

In addition to spatial location and energy signals, each received event causes the detector module to issue a trigger signal. The trigger signals from all the detector modules are conveyed to and received by a common coincidence detector. The common coincidence detector determines whether radiation events are within a temporal coincidence window of each other. If two, and only two, radiation events are within a coincidence window, they are deemed coincident events generated from the same electron-positron annihilation event. Signals representing coincident events are retained and used to reconstruct images. Radiation events that do not represent coincident events are discarded.

A typical large PET scanner may have about 20-30 radiation detector modules arranged to surround the subject. The market trend is to decrease the size of each detector cell and increase the number radiation detector modules. As the number of radiation detector modules is increased, the number of signals conveyed to the coincidence detector at any given time increases. As a consequence, the complexity of the coincidence detector logic increases (e.g., the number of inputs and associated wires increases), rendering conventional approaches unattractive and even impractical. In light of the aforementioned deficiencies, there is a need for an improved technique that facilitates overcoming these deficiencies.

In one aspect, an imaging system having a scalable event processing architecture includes a plurality of detector modules arranged around an associated imaging region to detect radiation events emitted from a subject disposed within the imaging region; a plurality of sets of processing elements, each set including processing elements of at least one of the plurality of radiation detector modules, each processing element time-stamping an associated detected radiation events; and inserting the time-stamped event into a chronological position within a data stream of events; and coincident detecting circuitry that receives the chronologically ordered stream of events and detects coincident pairs of events therein for use in reconstructing one or more associated images of the object.

One advantage includes processing radiation events detected by an imaging scanner with a large number of detector modules.

Another advantage resides in improved data flow and processing efficiency.

Another advantage lies in simplified data transmission.

Still further advantages will become apparent to those of ordinary skill in the art upon reading and understanding the detailed description of the preferred embodiments.

The drawings are only for purposes of illustrating embodiments and are not to be construed as limiting the claims. Wherein the drawings show:

Figure 1:
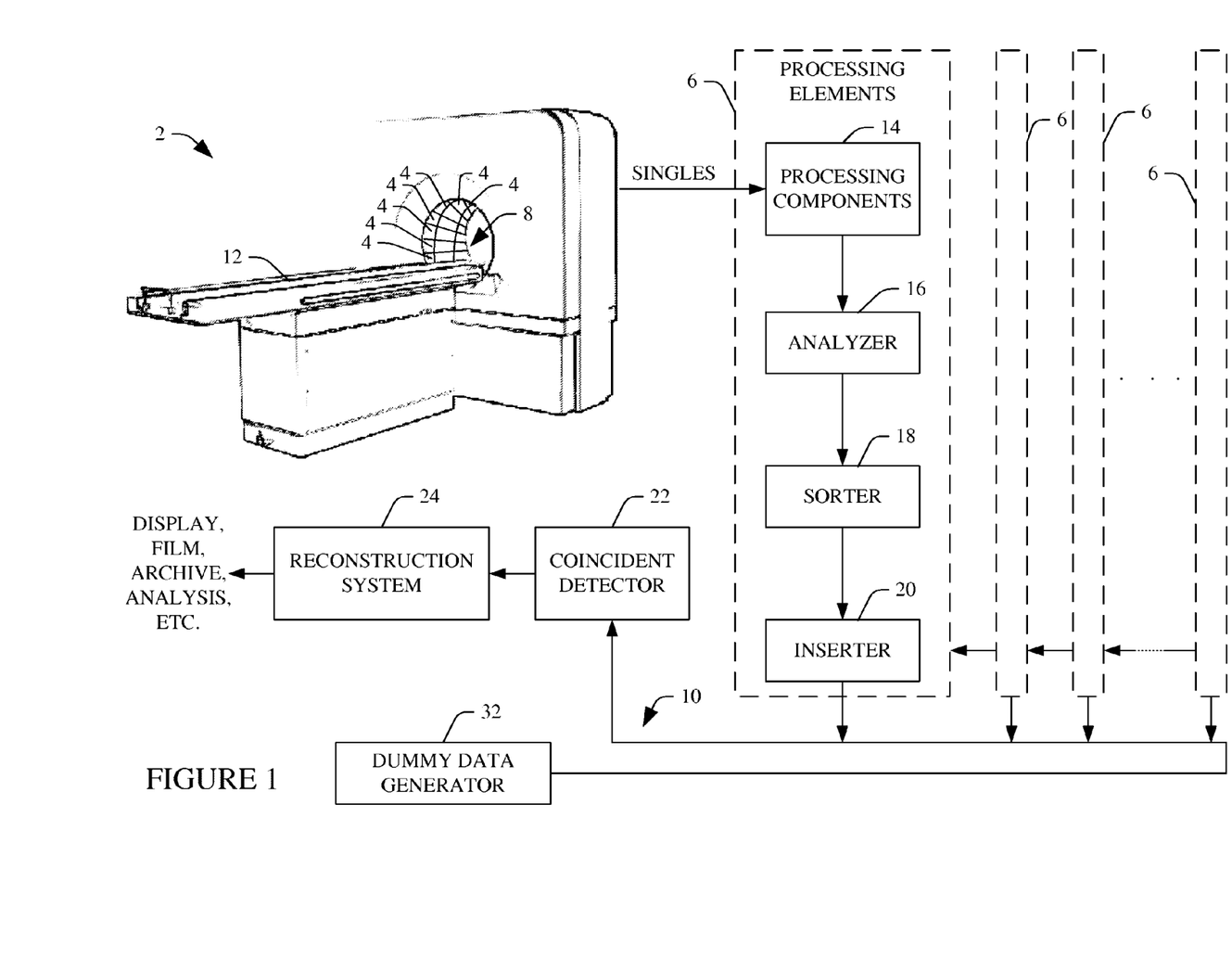
FIG. 1 illustrates a medical imaging system that employs a scalable processing architecture.

FIG. 1 illustrates a medical imaging system 2 (e.g., a positron emission tomography (PET) scanner) that employs a scalable processing architecture. The system 2 includes a plurality of radiation detector modules 4, each associated with one or more processing elements 6 and each arranged around an imaging region 8. The modules 4 are positioned to form one or more rings of radiation detectors that detect radiation events (e.g., gamma rays) occurring within the imaging region 8. Each processing element 6 includes circuitry that processes and packages detected radiation events (or singles) and chronologically inserts representative packets into a data stream or bus 10 for downstream processing (e.g., to detect coincident singles) and reconstruction into one or more images. Since processing and packaging singles and inserting corresponding packets occurs at the processing element level, the system 2 is easily scaled through the number of modules 4 employed and/or the number of processing elements 6 associated with each module 4. The system 2 also includes a patient couch or support mechanism 12 for positioning a subject (e.g., a human) in the imaging region 8 before, during and/or after imaging (e.g., two dimensional and three dimensional).

In preparation for an imaging with the system 2, a radiopharmaceutical is administered to the subject. The subject is suitably positioned within the imaging region 8. The radiopharmaceutical undergoes radioactive decay, which results in an emission of a positron. The positron interacts with one or more nearby electrons and annihilates, which produces two oppositely directed gamma rays having energies of about 511 keV each. The two oppositely directed gamma rays strike opposing detector modules 4 concurrently at substantially the same time. Because positions not originating equidistant from a pair of detectors travel different distances, albeit at about the speed of light, there is typically a slight time offset between coincident events.

A typical detector module 4 includes one or more scintillation crystals (not shown). Each scintillation crystal produces a scintillation of light when struck by a radiation event such as a gamma ray produced from positron annihilation. The light produced by each crystal is received by one or more photodetectors (not shown) associated with a corresponding processing element 6. Each of the photodetectors of the processing element 6 converts the light into a single, or a representative electrical signal. Of course, solid state detectors which generate the electrical signals directly in response to receive radiation and other types of detection systems are also contemplated.

The resulting singles from the one or more photodetectors are concurrently conveyed and processed by one or more processing components 14 over parallel channels. Suitable pre-processing includes signal amplification, filtering, and/or conditioning. The pre-processed singles are then digitized. The resulting digital singles are further processed, for example, to energy-correct and/or time-correct (e.g., time walk, offset correction) each single, and/or energy gate each single to filter singles associated with an energy outside of a predetermined energy window (e.g., singles deemed to be noise, scatter . . . ). Buffers and/or other storage medium can be used to facilitate pre-processing, digitizing, and/or further processing of the singles.

For each processing element 6, the processed singles are aggregated by an analyzer 16, which determines various characteristics of each single. For instance, the analyzer 16 determines a time (e.g., time stamp) when each event was received, an identification of the crystal that received each event, an energy of each event, one or more coordinates indicating a position at which each event was received, etc. The analyzer 16 also facilitates generating a packet for each single in which each packet includes at least a time stamp and optionally one or more of the crystal identification, the event energy value, the coordinates of the hit, and/or other information.

For each processing element 6, the packets and optionally other packets (e.g., packets forwarded from other processing elements 6, packets including a time stamp and system information, packet including a time stamp and null information . . . ) are time-sorted by a corresponding sorter 18, based on packet time stamps. Time-sorted packets associated with each processing element are inserted into a data stream 10 of packets by a corresponding inserter 20. In a preferred embodiment, the data stream 10 traverses each of the modules 4 and each processing element 6 within each module 4, module-by-module, one or more times.

As the data stream 10 traverses a particular processing element 6, its corresponding inserter 20 determines whether and where a packet should be inserted, and chronologically inserts each packet based at least in part on its time stamp into the stream 10, if the chronological position has not already passed. The inserter 20 may have to wait for the chronological position and/or for a subsequent pass of the data stream 10 in order to correctly insert a packet into the data stream 10. The inserter 20 may also convey the packet to another processing element 6 for insertion into the stream 10. For instance, where the correct chronological position of the packet within the data stream 10 has passed, the inserter 20 can forward the packet to a downstream processing element 6 that can insert the packet into the stream 10 at its chronological position. In another example, rather than waiting for the chronological position, the inserter 20 can convey the packet to an upstream processing element 6 for insertion into the data stream 10. Conveying the packet to another processing element 6 facilitates balancing load distribution and improves efficiency as well as compensating for any delays that result in an asynchronous set of singles.

The inserter 20 typically determines the chronological position of each packet by comparing time stamps of packets already in the data stream 10 with a time stamp of a packet to be inserted into the data stream 10. Employing this algorithm, a packet is inserted into the data stream when a succeeding packet is associated with a time stamp that is later than the time stamp of the packet being inserted and a preceding packet is associated with a time stamp that is earlier than the time stamp of the packet being inserted. The inserter 20 waits (e.g., including buffering packets as needed) to insert the packet into the data stream 10 or conveys the packet downstream, when the current packets traversing the processing element in the data stream 10 are associated with time stamps later than the time stamp of the packet to be inserted.

The inserter 20 continues to monitor the time stamps until the chronological position has arrived. In one instance, such monitoring is achieved on a packet-by-packet basis. In another instance, a time difference between a time stamp of a packet currently traversing the processing element 6 and the time stamp of the packet being inserted determines the frequency of packet checking. As the difference converges, the frequency of time stamp sampling increases to ensure the chronological position is located and the packet is inserted. For relatively large time stamp differences, the frequency is decreased in order to free processing cycles, which can improve overall performance. The inserter 20 either waits for a subsequent pass or forwards a packet when the succeeding and preceding packets in the data stream 10 are associated with time stamps later than the time stamp of the packet to be inserted.

The data stream 10 of sorted packets is conveyed to a coincident detector 22 that processes adjacent singles in order to identify pairs of substantially simultaneous coincident gamma ray detections, which correspond to electron-positron annihilation event pairs. This processing can include, for example, energy filtering (e.g., discarding radiation detection events outside of a selected energy filtering window disposed about 511 keV) and/or coincidence filtering (e.g., discarding radiation detection event pairs temporally separated from each other by greater than a selected time filtering interval or more than two events within a common window, random coincidence identification using a delayed windowing technique, etc.). It is to be appreciated that the coincident detector 22 may reside within a processing element 6, a reconstruction system, and/or other componentry. For example, in one instance a distributed coincidence check is performed at each processing element 6. The last processing element 6 of stream 10 discards the singles without coincident partners. The filtered stream 10 is provided to the reconstruction system. The coincidence check at the end of the stream 10 can be achieved via a FPGA on a board inside the reconstruction system and/or in the last processing element 6 of the chain.

When the coincident detector 22 identifies a coincident pair (e.g., adjacent singles within a coincident window), a line-of-response (LOR) connecting the coincident singles is generated. The electron-positron annihilation event is known to have occurred somewhere on the LOR. The spatial LOR and/or the pairs of coincident singles are conveyed to a reconstruction system 24, which reconstructs one or more images from this data using any suitable reconstruction algorithm. Examples of suitable algorithms include, but are not limited to, filtered backprojection and/or iterative backprojection with or without correction. The resulting reconstructed image can be displayed on a monitor, stored, printed on film, archived, conveyed to a clinician (e.g., a radiologist), etc.

Figure 2:
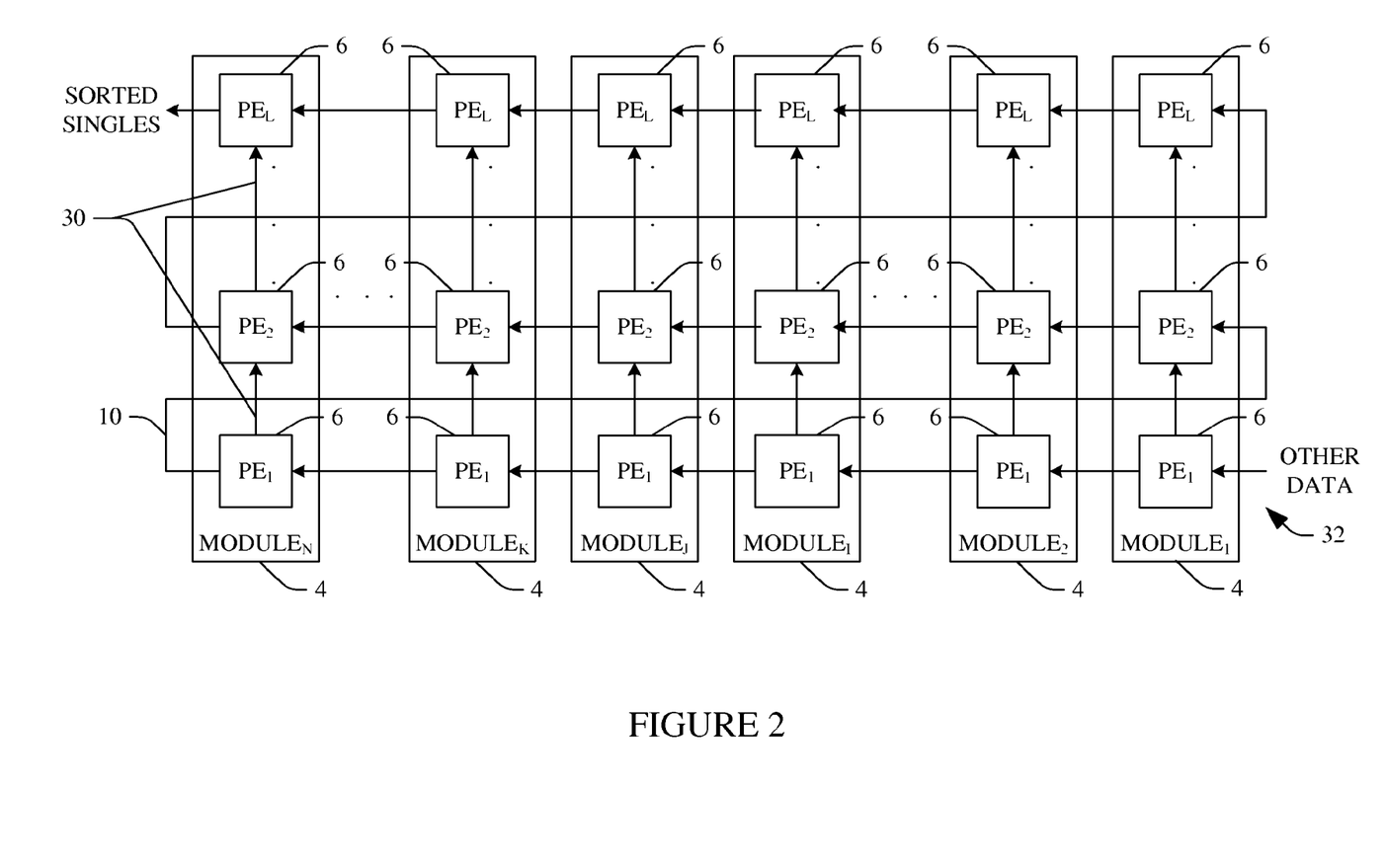
FIG. 2 illustrates a scalable data processing architecture for chronologically inserting singles into a data stream based on time stamps.

FIG. 2 illustrates an exemplary scalable data processing architecture for chronologically inserting singles (packaged as packets) into a data stream 10 based on associated time stamps. In this example, the system 2 includes N modules 4, each of which includes L processing elements 6, where N and L are integers equal to or greater than one. The data processing architecture of the system 2 is scaled by suitably selecting N and L.

When a radiation event (e.g., a gamma ray from a positron annihilation) is received by (strikes) one of the modules 4, transducing componentry (e.g., one or more scintillators, photodetectors, solid state detectors, . . . ) associated with the processing elements 6 generate one or more representative electrical signals, or singles. In addition, each processing element 6 determines various characteristics of the corresponding singles and packages each single into a packet that includes at least a time stamp indicating the time the event was received, and optionally one or more of an identification of the detector that received the event, an energy of the event, one or more coordinates indicating a position of the event, and/or other information.

Each processing element 6 time-sorts corresponding packets and chronologically inserts them into the data stream 10. In a preferred embodiment, the chronological position is located by comparing time stamps of packets already in the data stream 10 with a time stamp of a packet being inserted into the data stream 10. The chronological position of any given packet being inserted into the data stream 10 is between a packet with a time stamp earlier than the time stamp of the packet being inserted and a packet with a time stamp later than the time stamp of the packet being inserted.

In an illustrated embodiment, each processing element 6 is operatively coupled, via the data stream 10, to at least one neighboring processing element 6 residing in a different radiation module 4. In this configuration, substantially all of the processing elements 6 are connected to two neighboring processing elements 6, an upstream processing element 6 residing in a preceding radiation detector module 4 and a downstream processing element 6 residing in a downstream radiation detector module 4.

By way of example, a processing element "$PE_1$" residing within a radiation detector module "$MODULE_J$" communicates with a processing element "$PE_1$" residing within a succeeding radiation detector module "$MODULE_K$" and a processing element "$PE_1$" residing within a preceding radiation detector module "$MODULE_I$." In another example, a processing element "$PE_2$" residing within a radiation detector module "$MODULE_1$" communicates with a processing element "$PE_2$" residing in a succeeding radiation detector module "$MODULE_2$" and a processing element "$PE_1$" residing within a preceding radiation detector module "$MODULE_N$." Exceptions at least include a processing element "$PE_1$" residing within the radiation detector module "$MODULE_1$" and a processing element "$PE_L$" residing within the radiation detector module "$MODULE_N$." These two processing elements 6 represent an initial processing element and an end processing element and both typically are only associated with one neighboring processing element 6 residing in a different radiation module 4.

The data stream 10 is depicted in FIG. 2 as a single path that serially traverses all the processing elements 6, module-by-module. However, it is to be appreciated that various other data paths are contemplated. For example, the processing elements 6 and/or the radiation detector modules 4 can be partitioned into multiple groups, wherein each grouping can include its own path and/or share one or more processing elements 6 (e.g., a beginning processing element 6, an ending processing element 6 . . . ). In another example, one or more of the processing elements 6 may be excluded from the data stream 10. For instance, a non-functional or malfunctioning processing element 6 can be skipped over. Essentially, any number of data paths can be formed by variously connecting the processing elements 6 in any suitable manner.

Optional data paths 30 are formed within each radiation detector module 4 by coupling the processing elements 6 in each radiation detector module 4. The paths 30 are used as bypass paths to move packets between processing elements 6, for example, to move a packet to a processing element 30 that can more efficiently insert the packet into a chronological location in the stream 10. For instance, each processing element 6 can send data to the following processing element 6 via the stream 10 as described above. This would disrupt the order of the packets in the stream 10, but the processing elements 6 could then use one or more of the data paths 30 to forward at least part of late arriving data to a suitable processing element 6 to compensate for the disruption.

In another example, with an embodiment in which the scanner 2 utilizes photomultiplier tubes (PMTs), a single may be delayed due to varying mapping rates associated with mapping detected events to crystals. Such delay may result in a scenario in which the corresponding packet can only be inserted into its chronological position in the data stream 10 by being conveyed to a downstream processing element 6 that has not already seen the chronological position in the data stream 10 pass and/or by waiting for a subsequent pass of the data stream 10 in a multi-pass architecture. In the former case, the packet is forwarded over one or more of the paths 30 to a suitable processing element 6 that can insert the packet into its chronological location within the data stream 10. In the later case, the packet is buffered until it can be inserted into its chronological location within the data stream 10.

In an embodiment in which the scanner 2 utilizes digital photodiodes, such compensation associated with mapping events to crystals typically is not needed since a substantially similar amount of time is consumed to determine each position of each event on each associated crystal. As a result, mapping the event to the position typically does not introduce varying delays from single to single. In these instances, the paths 30 can be used to introduce delays. For example, packets at the end of the ring wait a longer period of time before being inserted into the data stream 10. As a consequence, a buffer may be required to buffer the packets until stream 10 traverses the associated radiation detector module 4. The packets can be pushed through the paths 30 to facilitate distributing the packets upstream for insertion into the data stream 10 in a more uniform manner. Using the paths 30 as such can mitigate buffer overflow and balances load.

In addition to packets with singles related information, packets with other information are also inserted into the data stream 10. For instance, one or more dummy packets, each with at least a time stamp, are inserted into the stream 10. As depicted at 32, such packets are at least inserted into the stream 10 as one or more leading packets. These packets facilitate locating chronological positions within the stream 10. For instance, when employing an algorithm that locates a chronological position within the stream 10 by comparing time stamps of adjacent packets already in the stream 10 with the time stamp of the packet being inserted into the stream 10, providing a leading dummy packet with at least a time stamp provides a packet, which would not be there otherwise, for such comparison.

Although FIG. 2 illustrates dummy packet insertion at 32, it is to be understood that such packets can be inserted at any time and/or at any position within the data stream 10. Typically, the time stamps of these packets are not arbitrary in order to mitigate disrupting the chronological sequence of the data stream 10. Synchronization packets are also inserted periodically at 32 to prevent the bus from being blocked. The ability to insert dummy packets into the data stream 10 is leveraged to ensure a continuous stream of packets traversing each processing element 6 and mitigate situations wherein the comparison cannot be executed. In other instances, additional information such as system information can be included in one or more "dummy" packets. For example, a patient support position retrieved from a sensor at a particular time, error logs, maintenance scheduling, temperatures, and the like can be incorporated within a packet along with the time stamp.

The resulting time-sorted data stream of singles is conveyed to coincident detection circuitry 22, which processes adjacent time-sorted singles and identifies pairs of substantially simultaneous gamma ray events. The coincident detection circuitry may reside external (e.g., in a reconstruction system) from the modules 4 and/or within one or the processing elements 6 (e.g., the last processing element 6 in the data stream 10). Implementing coincident detection circuitry within a processing element 6 enables filtering of non-coincident singles from the stream 10. As a result, non-coincident singles can be discarded prior to conveying the singles to the reconstruction system. The foregoing reduces pipeline load and mitigates having to coincident check in the reconstruction system.

Figure 3:
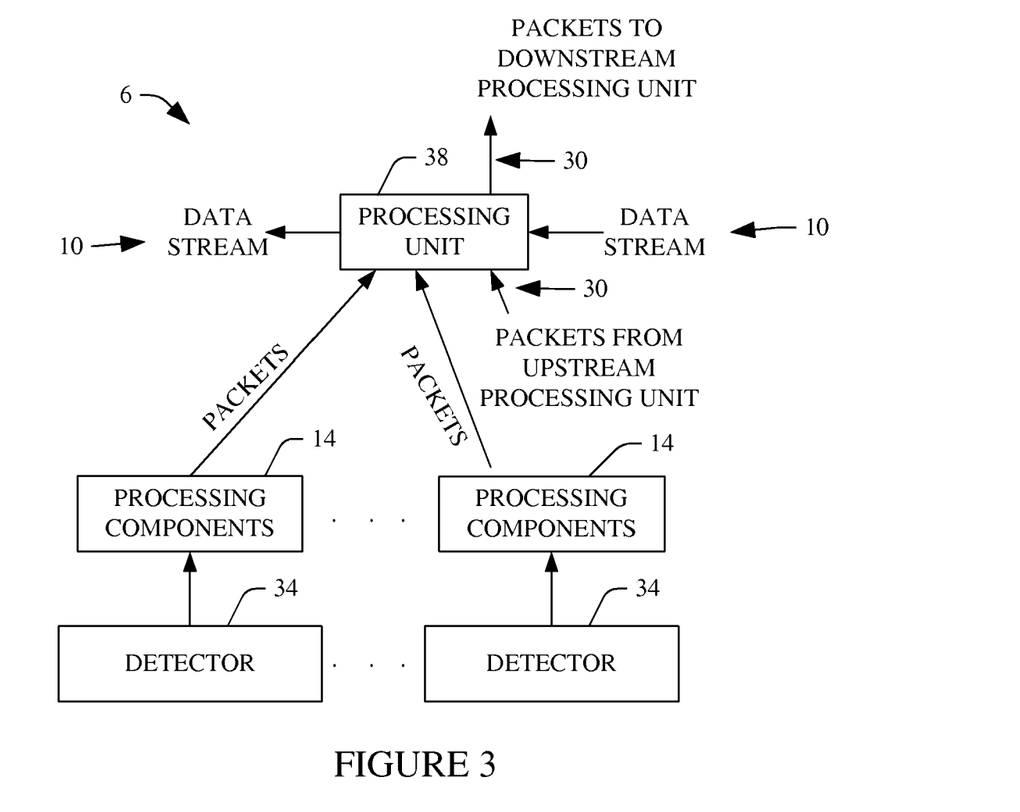
FIG. 3 illustrates a processing element architecture for processing and chronologically inserting singles into a data stream based on time stamps.

FIG. 3 illustrates an exemplary processing element architecture. As depicted, each processing element 6 is associated with one or more detectors 34. The detectors 34 generate a corresponding single corresponding to each detected radiation event. The singles are optionally parallel processed via the processing components 14 to a suitable format for insertion into the stream 10 by a processing unit 38. Such processing includes one or more of amplification, filtering, conditioning, digitization, various corrections, and/or energy gating. In addition, the processing components 14 determine various characteristics related to the singles such as an identity of the detector that received the event, an energy of the event, coordinates of the hit on the radiation detector module 4, and a time stamp indicating the time of the hit can be determined and associated with each single, for example, in a packet.

The processing components 14 asynchronously stream packets to the processing unit 38, which time-sorts the packets and inserts them into the data stream 10, based on time stamp. The processing unit 38 also receives packets from other processing elements 6 via the path 30. These packets are sorted along with the packets from the processing components 14. It is to be appreciated that each processing unit 38 can include dedicated and/or multi-functional logic, including one or more Programmable Gate Arrays (PGAs), one or more Application Specific Integrated Circuits (ASICs) and/or the like.

Upon receiving the packets, the processing unit 38 either chronologically inserts each packet into the data stream 10 and/or conveys packets to other processing units 6 via the path 30 for insertion. As discussed previously, the chronological position is determined by comparing time stamps of packets already in the stream 10 with a time stamp of a packet being inserted into the stream 10. When the time stamps of adjacent packets in the stream 10 are both earlier than the time stamp of the packet being inserted, the processing unit 6 holds (e.g., buffers, stores . . . ) the packet until the chronological position passes. When the time stamp of one packet in the stream 10 is earlier than the time stamp of the packet being inserted and the time stamp of a next packet in the stream 10 is later than the time stamp of the packet being inserted, the processing unit 38 inserts the packet between the those two packets in the stream 10. When the time stamps of adjacent packets in the stream 10 are both later than the time stamp of the packet being inserted, the processing unit 38 forwards the packet to a processing unit 38 in a downstream processing element 6 and/or inserts the packet during a second pass of the stream 10.

Figure 4:
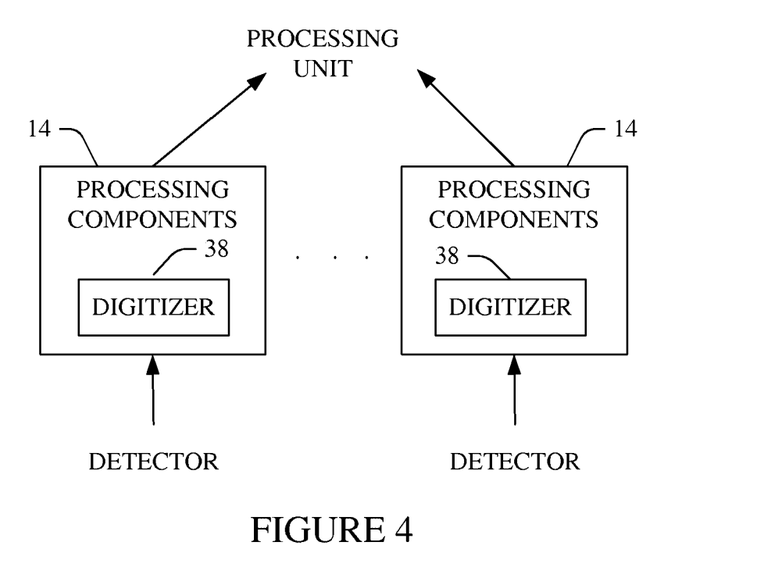
FIG. 4 illustrates a processing element with digitizers that digitize electrical signals received from one or more associated detectors.
Figure 5:
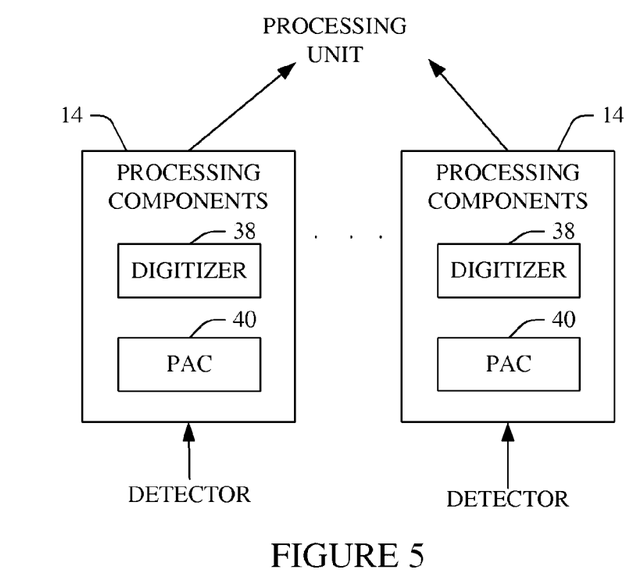
FIG. 5 illustrates a processing element with Pulse Amplification and Conditioning (PAC) circuitry that amplifies and/or conditions signals received from one or more associated detectors.
Figure 6:
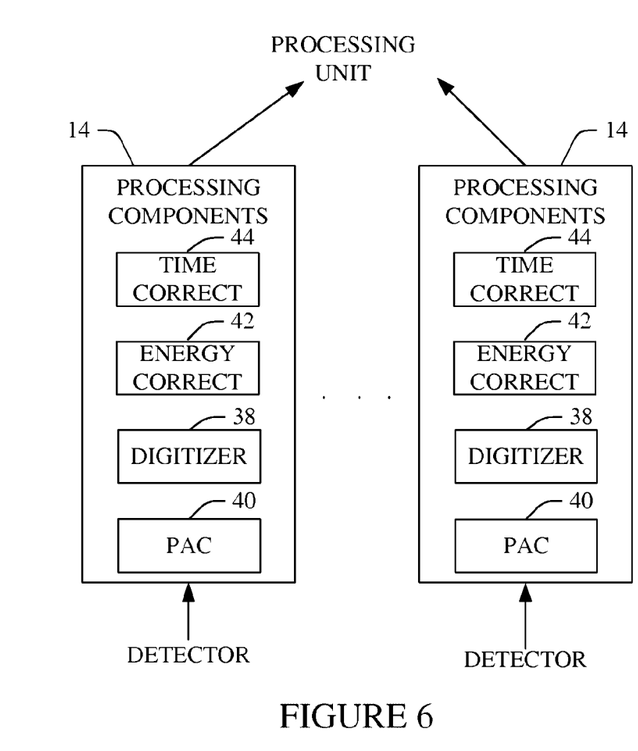
FIG. 6 illustrates a processing element with componentry that energy-corrects and/or time-corrects singles.
Figure 7:
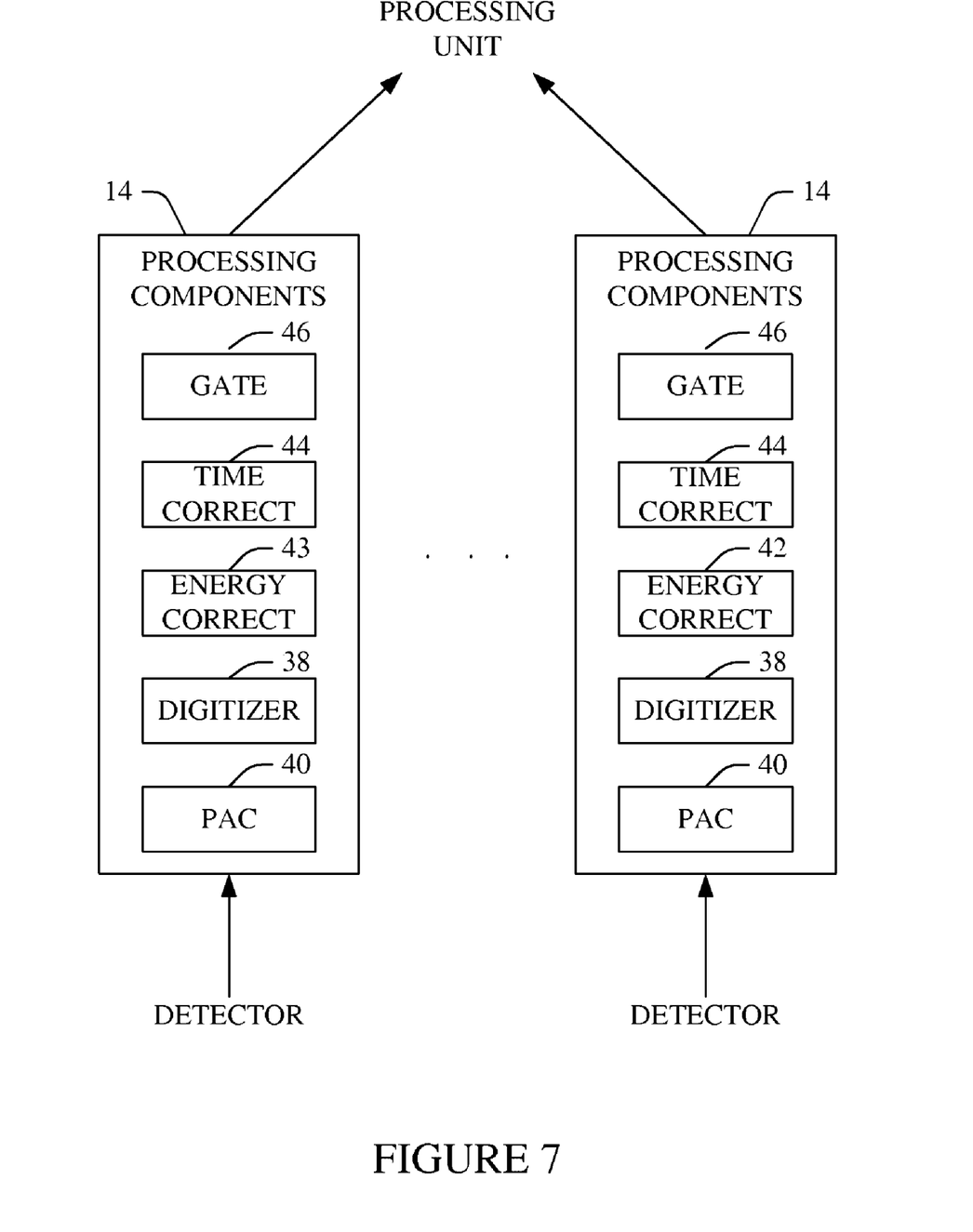
FIG. 7 illustrates a processing element with componentry that energy-gates singles.

FIGS. 4-7 illustrated suitable processing logic executed by the processing components 14 in accordance with various embodiments. As illustrated in FIG. 4, in one embodiment each processing component 14 includes a digitizer 38 that digitizes an electrical signal conveyed from a corresponding detector. FIG. 5 additionally shows optional Pulse Amplification and Conditioning (PAC) circuitry 40 that amplifies (e.g., to increase the resolution or dynamic range) and/or conditions the signals from the photo or other detectors 34. FIG. 6 illustrates another embodiment which includes an element 42 that energy-corrects each single to scale for apparent energy variations and an element 44 that time-corrects (e.g., time walk, offset correction) each single to adjust for relative processing time and transmission time differences among the detectors. FIG. 7 shows an embodiment having a gate 46 used to threshold energy levels. The gate 46 compares measured event energy with a predetermined energy window and only passes events with energy levels within the window. Events with energy levels out of the window are deemed noise, scatter, etc. and are discarded.

Figure 8:
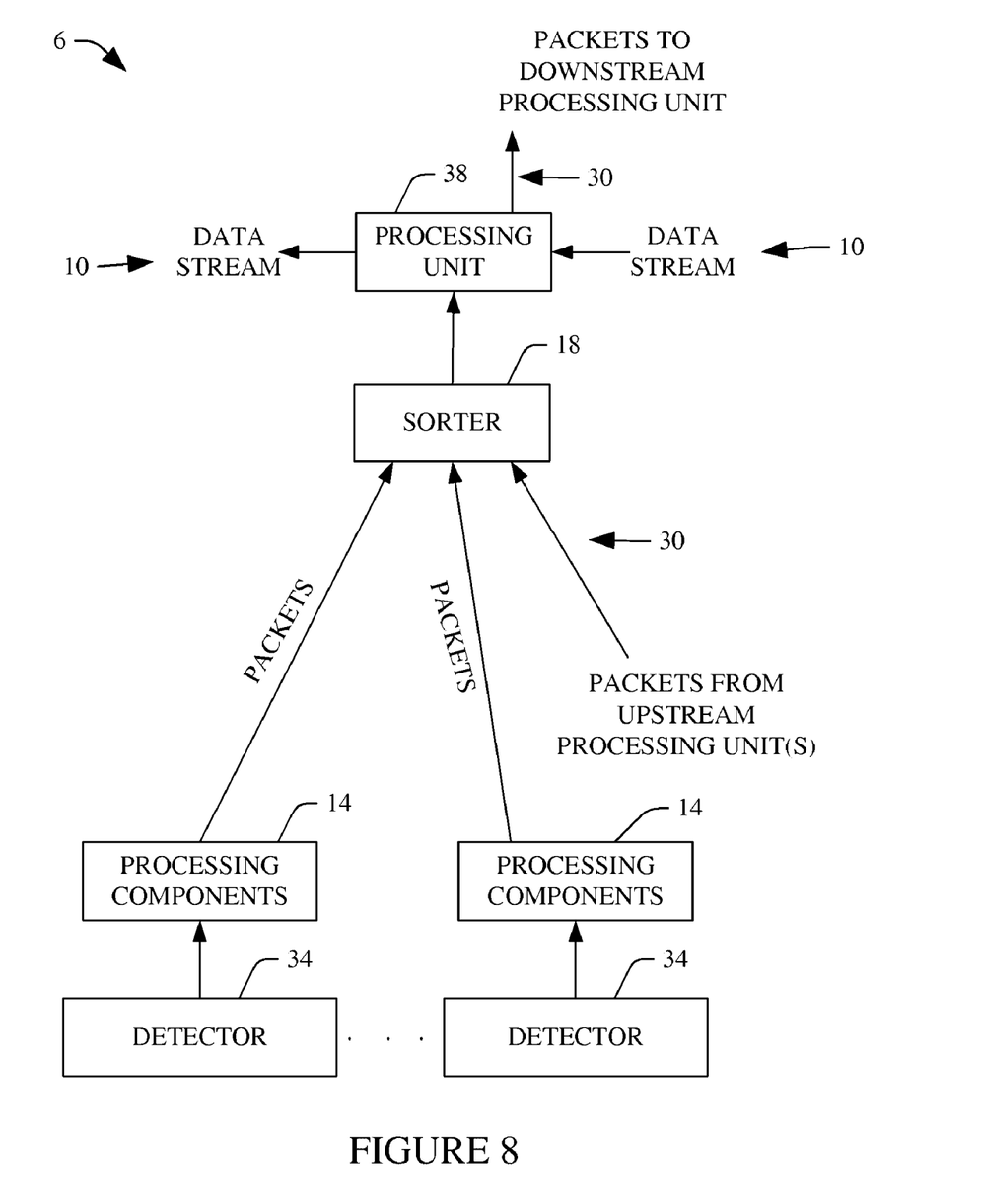
FIG. 8 illustrates a processing element with a sorter that time-sorts packets.
Figure 9:
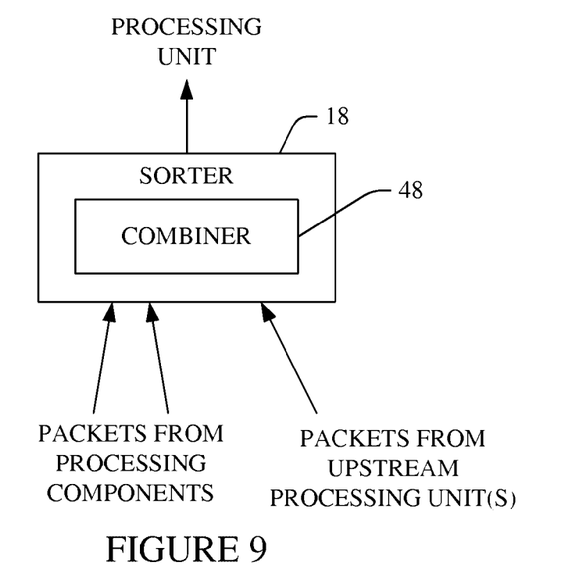
FIG. 9 illustrates a sorter having a many-to-one combiner that receives all packets and time-sorts them for insertion into the data stream.

FIG. 8 illustrates an embodiment in which the sorter 18 time-sorts packets from the processing components 14 and/or other processing elements 6 and conveys them to the processing unit 38 for insertion into the stream 10. The sorter 18 can employ various sorting techniques. For example, the sorter 18 can include one or more components (e.g., multiplexers, buffers . . . ) that facilitate sorting packets in chronological order based on time stamp. In one instance, the sorter 18 includes a single many-to-one combiner 48 that receives all packets and sorts them for insertion into the data stream 10. This is illustrated in FIG. 9.

Figure 10:
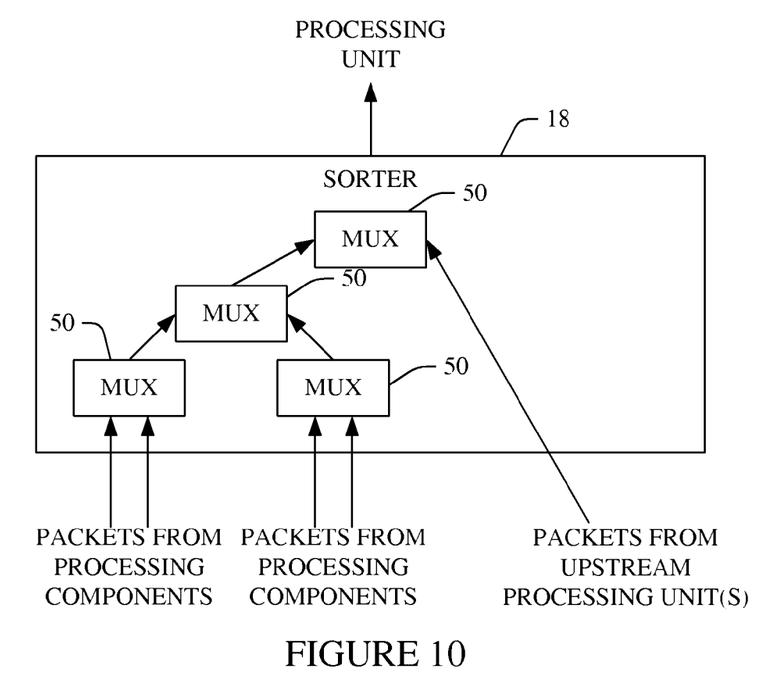
FIG. 10 illustrates a sorter with tree-type pipeline that time-sorts pairs of packets in parallel via a plurality of multiplexers.

FIG. 10 illustrates a tree-type sorting pipeline. With this pipeline, pairs of packets are sorted in parallel via a plurality of multiplexers 50 ("MUX 50"). Sorted pairs from two or more multiplexers 50 are fed to another multiplexer 50 that sorts the received packets. The steps of receiving sets of packets, sorting them, and conveying the sorted set to another multiplexer 50 continues until all packets are sorted and ready to be inserted into the stream 10. For sake of brevity, FIG. 10 illustrates three levels of sorting; however, it is to be appreciated that any number of levels of sorting are contemplated. In addition, suitable multiplexers are not limited to two-to-one combining operations.

Figure 11:
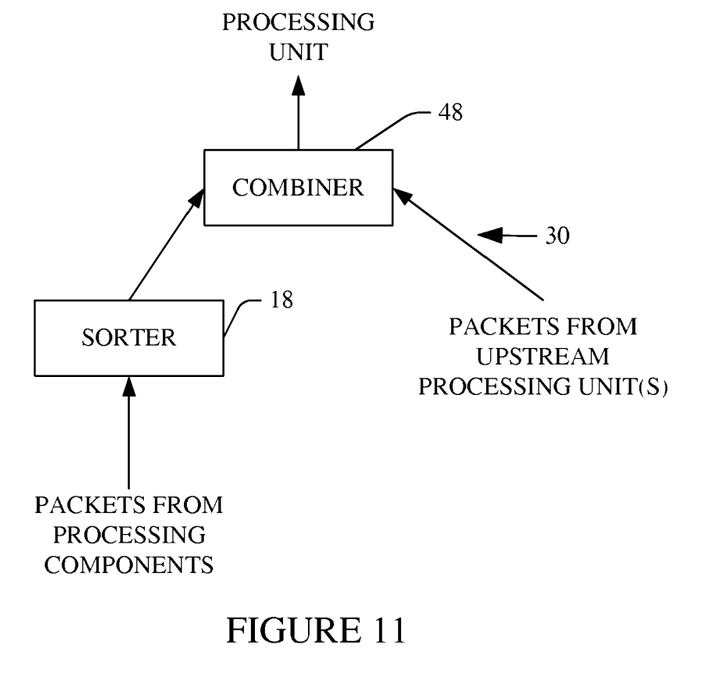
FIG. 11 illustrates a processing element with a combiner that time-sorts and combines streams of time-sorted packets.
Figure 12:
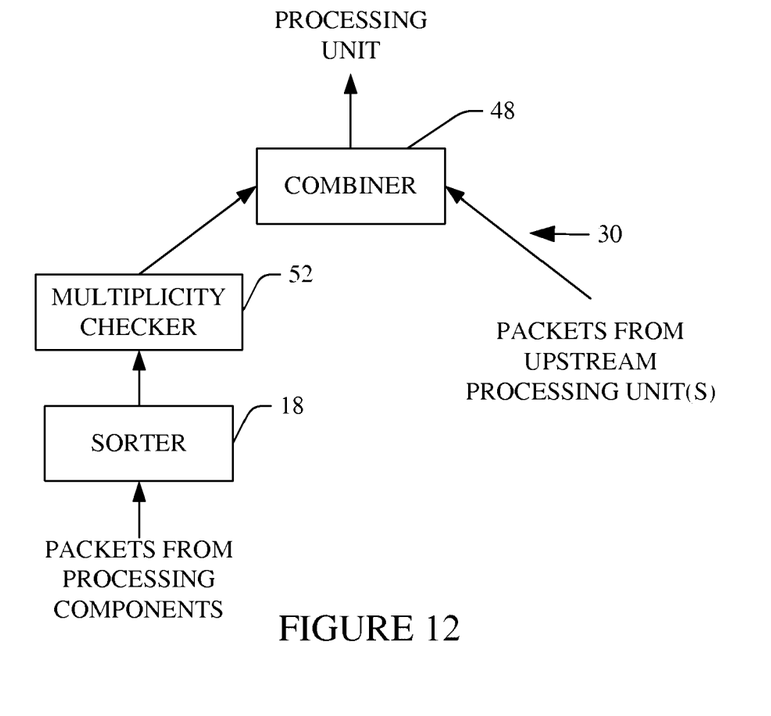
FIG. 12 illustrates a processing element using a multiplicity checker.

FIG. 11 illustrates an alternative embodiment in which the sorter 18 is used to sort and combine packets from the processing components 14 and the resulting sorted packets are sorted and combined with packets received via path 30 by the combiner 48, which resides outside of the sorter. Although the combiner 48 is depicted as a distinct component, it is to be appreciated that the combiner 48 can alternatively reside within the processing unit 38. FIG. 12 illustrates an embodiment having an optional multiplicity checker 52. The multiplicity checker 52 typically is used with PMT-based systems in which the processing elements receive data from overlapping portions of the detector. For example, in PMT-based systems a signal from one PMT is fed to several adjacent channels (i.e. overlapping 7-rings of the Anger logic). This results in a possible detection of the same event by more than one channel. The multiplicity checker 52 facilitates locating and resolving processing related issues with such detection by multiple channels.

It is to be understood that the foregoing examples are provided for explanatory purposes and are not limiting. Various other configurations for sorting and combining singles and/or packets are also contemplated.

Figure 13:
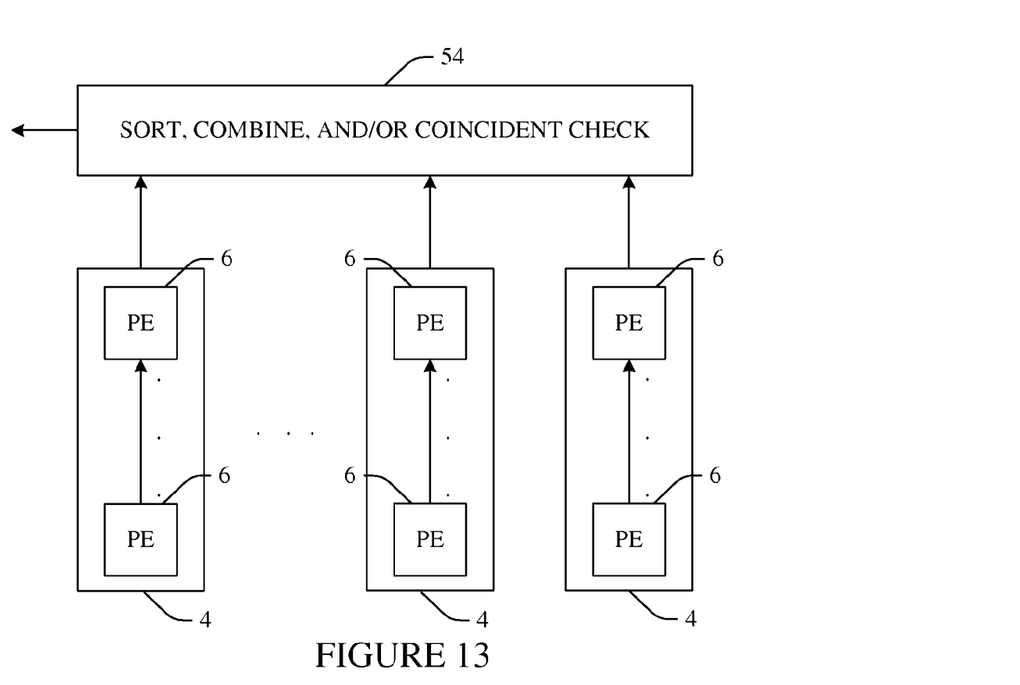
FIG. 13 illustrates an alternative axial topology processing architecture.

FIGS. 13-16 illustrate various other processing architectures used with the scanner 2. FIG. 13 depicts an axial readout topology. This topology includes the plurality of radiation detector modules 4, each include one or more processing elements 6. The processing elements 6 residing within each module 4 are connected together to form a plurality of individual serial data paths to a common component 54 that sorts and combines packets and/or coincident detects. For example, if the scanner 2 were configured with X radiation detector modules 4 (where X is an integer equal to or greater than one), there would be X data paths, one from each module 4, sourcing singles to the common component 54.

Figure 14:
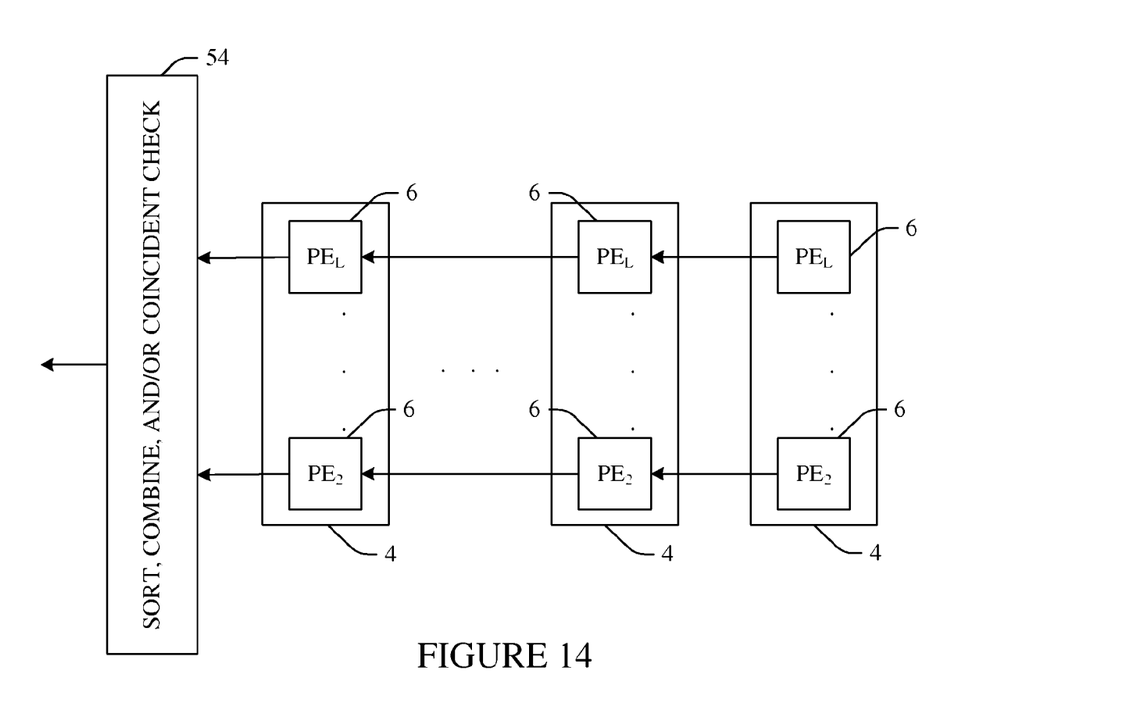
FIG. 14 illustrates an alternative radial topology processing architecture.

FIG. 14 depicts a radial readout topology. This topology also includes the plurality of radiation detector modules 4, each with one or more processing elements 12. In this example, processing elements 6 residing in different (e.g., adjacent) radiation detector modules 4 are connected together to form a plurality of individual serial data paths to the common component 54. In this embodiment, the number of processing elements 6 within each module 4 determines the number of data paths to the common component 54. For example, if each radiation detector module 4 includes Y processing elements 6 (where Y is an integer equal to or greater than one), then there would be Y data paths sourcing singles and/or packets to the common component 54.

Figure 15:
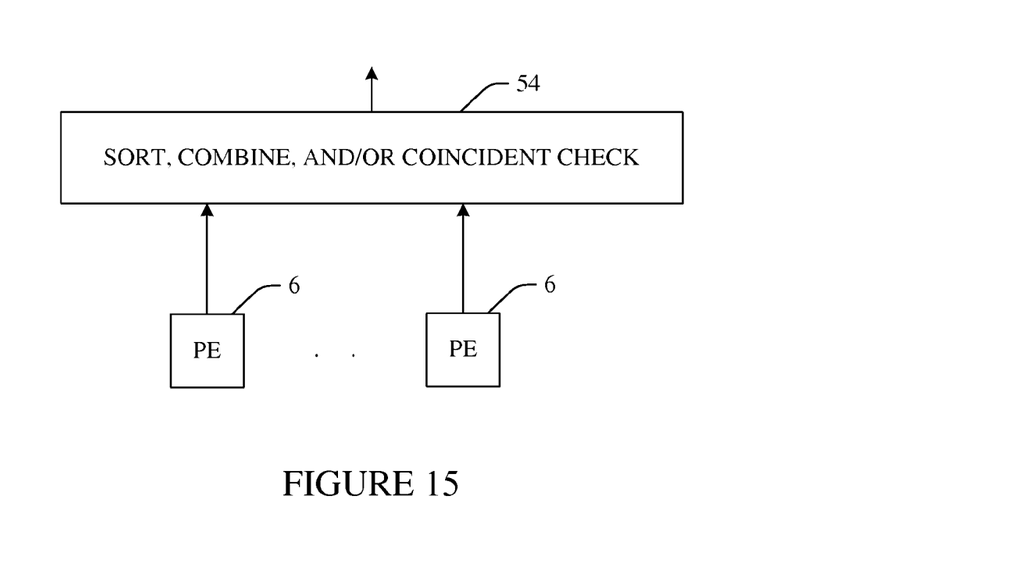
FIG. 15 illustrates an alternative star topology processing architecture.

FIG. 15 illustrates an star topology architecture in which each processing element 6 individually conveys singles and/or packets to the common component 54, which performs the above discussed processing operations in a single component or component array rather than with distributed components.

Figure 16:
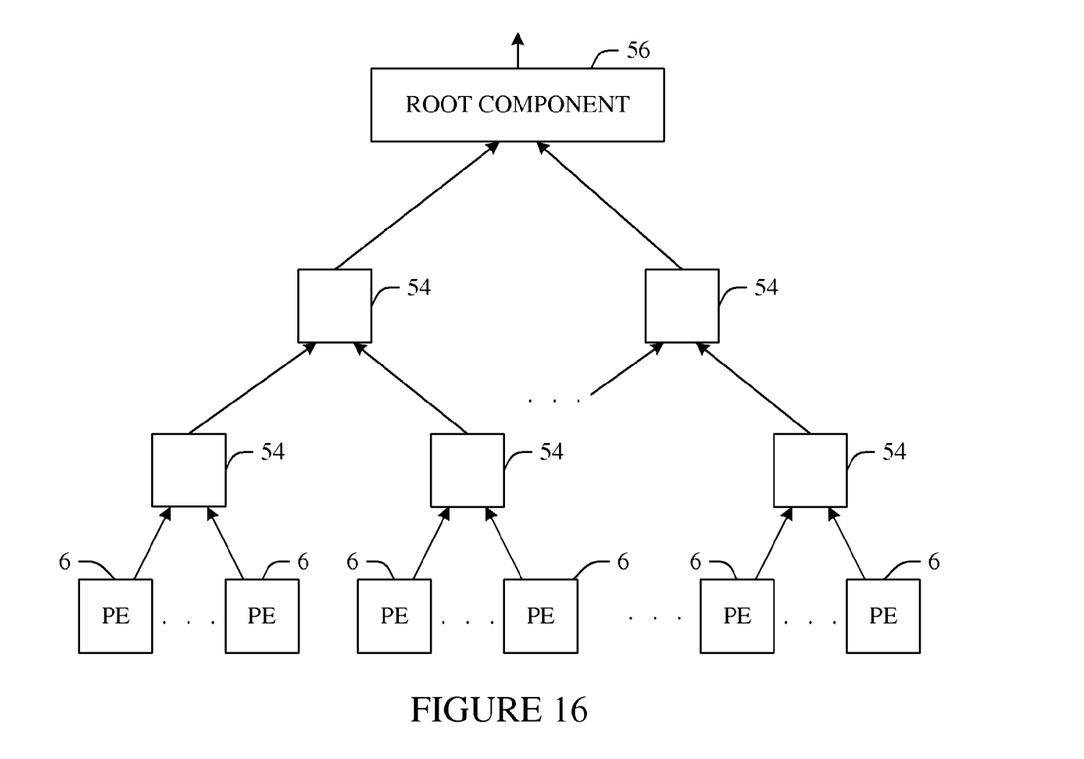
FIG. 16 illustrates an alternative distributed topology processing architecture.

FIG. 16 illustrates a distributed topology approach, wherein singles and/or packets from two or more processing elements 6 are sorted, combined, and coincidence checked via a plurality of distributed sort, combine and/or coincident check components 54 that converge to a single root component 56.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. An imaging system having a scalable event processing architecture, comprising:
a plurality of detector modules arranged around an associated imaging region to detect radiation events emitted from a subject disposed within the imaging region, each module has a plurality of processing elements;
a data stream which serially traverses the processing elements transporting chronologically ordered radiation events;
each of the plurality of processing elements performing the processing steps of:
time-stamping detected radiation events; and
inserting the time-stamped radiation events into a chronological order within the data stream of events;
the data stream transporting the chronologically ordered radiation events through each module a plurality of times;
a plurality of data paths that connect the plurality of processing elements within each module to selectively convey one or more time-stamped radiation events to an upstream or downstream one of the processing elements; and
coincident detecting circuitry that receives the chronologically ordered stream of time-stamped radiation events and detects coincident pairs of time-stamped radiation events therein for use in reconstructing one or more associated images of the object.

2. The imaging system as set forth in claim 1, further including one or more bypass data paths that move time-stamped events from a first of the processing elements to a second of the processing elements that is downstream of the first for insertion into the data stream downstream to compensate for a delay.

3. The imaging system as set forth in claim 1, wherein each processing element includes:
a Pulse Amplification and Conditioning (PAC) that amplifies and conditions the detected event;
a digitizer that digitizes the detected event;
an energy correction element that energy-corrects the detected event;
a time correction element that time-corrects the detected event; and,
a gate that compares the detected event to an energy window to determine whether to discard the detected event as noise.

4. The imaging system as set forth in claim 1, wherein each detector module includes at least a first processing element and a second processing element, the data stream serially traversing the first processing elements and then serially traversing the second processing elements.

5. The imaging system as set forth in claim 1, wherein each detector module includes at least a first processing element and a second processing element, and a third processing element, the data stream serially traversing the first processing elements and then serially traversing the second processing elements and then serially traversing the third processing elements and the data paths of each detector module connecting the first, second, and third processing units of said detector module.

6. An imaging system having a scalable event processing architecture, comprising:
   a plurality of detector modules arranged around an associated imaging region to detect radiation events emitted from a subject disposed within the imaging region;
   a plurality of sets of processing elements, each set including processing elements of at least one of the plurality of radiation detector modules, each processing element:
      digitizing detected radiation events;
      time-stamping the detected radiation events; and
      inserting event packets, each event package including one of the time-stamped events, into a chronological position within a data stream of the time-stamped events; and
   a dummy packet inserting component that inserts time stamped dummy packets which contain non-event information chronologically into the data stream such that a continuous flow of packets through each of the processing elements is ensured and such that locating chronological positions within the stream of events for event packet insertions is facilitated; and
   coincident detecting circuitry that receives the chronologically ordered stream of packets and detectors coincident pairs of events in the event packets for use in reconstructing one or more associated images of the object.

7. The imaging system as set forth in claim 6, wherein the data stream connects the processing elements in a plurality of parallel paths, and further including a sorter that receives time-stamped events from a plurality of the parallel paths and aggregates the events based on corresponding time stamps.

8. The imaging system as set forth in claim 6, wherein the data stream is branched and further including one or more multiplexers which receive time stamped events from a plurality of branches of the data stream and chronologically sorts the time stamped events.

9. The imaging system as set forth in claim 6, wherein the processing elements are configured in one of an axial readout, a radial readout, a star, and a distributed topology.

10. The imaging system as set forth in claim 6, wherein the dummy packet inserting component is different from the detector modules and the dummy packets do not include radiation event data.

11. The imaging system as set forth in claim 6, wherein the dummy packets carry one or more of: patient support position information, error logs, maintenance information, temperature, and system information.

12. A method for sorting radiation events prior to coincident detectors, the method comprising:
   detecting radiation events at each of a plurality of radiation detection modules;
   generating a time-stamped packet representing each event;
   inserting each packet into a stream of packets in a corresponding chronological order, the stream serially traversing the detector modules;
   passing the stream through each module a plurality of times; and
   examining the stream of packets for coincident pairs.

13. The method as set forth in claim 12, further including:
   when packets in one pass of the stream have time stamps later than a packet to be inserted, inserting the packet in an earlier pass of the stream through the detector module.

14. The method as set forth in claim 12, wherein the radiation events are detected by a plurality of detector modules and each detector module includes at least first and second processing elements which generate the time-stamped packets and further including:
   serially passing the stream through the first processing elements of the detector modules, module-by-module, and subsequently passing the stream through the second processing element of the detector modules; and
   passing the time-stamped packets between the first and second processing elements such that the time-stamped packets are inserted into the stream in one of a first pass through each detector module and a second pass through the detector module.

15. The method as set forth in claim 12, further including:
   inserting time-stamped dummy packets containing non-event information into the stream to facilitate chronological ordering packets in the stream and to ensure a continuous stream of packets; and
   conveying dummy packets through the stream.

16. An imaging system for performing the method of claim 12.

17. A processor for sorting coincident events in medical imaging devices, comprising:
   one or more different sets of processing elements that are coupled to form a data path for carrying a stream of sorted packets;
   at least one inserter associated with each of the one or more different set of processing elements, each inserter:
      determines a chronological position in the stream for a packet being inserted,
      inserts the packet into the chronological position in the stream,
      computes a time difference between a time stamp of a packet currently traversing the inserter and a time stamp of the packet being inserted, and
      periodically monitors packets in the stream to locate the chronological position of the packet being inserted based on the time difference.

18. The processor as set forth in claim 17, wherein each inserter monitors packets in the stream on a packet-by-packet basis until the chronological position for the packet being inserted is detected.

19. The processor as set forth in claim 17, wherein the frequency of monitoring the packets in the stream increases as time difference decreases.

20. An imaging system comprising:
   a plurality of radiation detector modules disposed in one or more rings around an examination region, each module including an array of radiation detectors which produce signals indicative of radiation events and a plurality of processing elements, each processing element digitizes the radiation event signals, time stamps the digitized radiation event signals, forms time-stamped packets each including one of the digitized radiation event signals and an event location, and inserts the time-stamped radiation event packets chronologically in order in a packet stream;
   a packet stream path which connects the plurality of processing elements, the packet stream path running from a first of the processing elements on a given detector module and through a signal processing element on each of a plurality of others of the detector modules before running through a second of the processing elements on said given detector module;
   a plurality of intramodule packet paths, each of the intramodule packet paths connecting a pair of processing elements in the given detector module, such that the time-stamped radiation event events packets of the given detector module can be inserted into the packet stream in any of a plurality of passes of the packet stream through the given detector module;

a dummy packet inserting component connected to the packet stream, the dummy packet inserting component inserting time-stamped dummy packets into the data stream, the dummy packets carrying other than radiation event information; and a coincidence detector connected with the packet stream path to receive the packet stream, the coincidence detector detecting coincident pairs of radiation events from the time stamps of the time-stamped radiation event packets, the coincident pairs of radiation events defining lines of response to be used to reconstruct an image of a subject in the examination region.

21. The imaging system as set forth in claim 20, wherein the dummy packets carry one or more of: patient support position information, error logs, maintenance information, temperature, and system information.

22. The imaging system as set forth in claim 20, wherein each detector module includes at least a first processing element and a second processing element, the data stream serially traversing the first processing elements and then serially traversing the second processing elements.

23. The imaging system as set forth in claim 20, wherein each processing element includes an inserter which inserts the radiation event packets into the data stream, each inserter computes a time different between a time stamp of a packet currently traversing the inserter and a time stamp of the radiation event packet being inserted and periodically monitors packets in the stream to locate a chronological position of the radiation event packet being inserted based on the time difference, a frequency of monitoring the packets in the stream increasing as time difference decreases.

* * * * *